United States Patent
Wang et al.

(10) Patent No.: US 10,726,742 B2
(45) Date of Patent: Jul. 28, 2020

(54) 3D PRINTED METAMATERIAL TISSUE-MIMICKING PHANTOMS

(71) Applicant: Georgia Tech Research Corporation, Atlanta, GA (US)

(72) Inventors: Kan Wang, Atlanta, GA (US); Zhen Qian, Atlanta, GA (US); Chun Zhang, Atlanta, GA (US); Changsheng Wu, Atlanta, GA (US); Ben Wang, Atlanta, GA (US); Mani A. Vannan, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 222 days.

(21) Appl. No.: 15/804,737

(22) Filed: Nov. 6, 2017

(65) Prior Publication Data
US 2018/0158372 A1  Jun. 7, 2018

Related U.S. Application Data

(60) Provisional application No. 62/417,462, filed on Nov. 4, 2016.

(51) Int. Cl.
| | | |
|---|---|---|
| *G09B 23/30* | (2006.01) |
| *B33Y 80/00* | (2015.01) |
| *A61B 34/10* | (2016.01) |
| *B29C 64/386* | (2017.01) |
| *A61F 2/24* | (2006.01) |
| *A61F 2/06* | (2013.01) |

(52) U.S. Cl.
CPC ............. *G09B 23/30* (2013.01); *B33Y 80/00* (2014.12); *A61B 2034/102* (2016.02); *A61F 2/06* (2013.01); *A61F 2/2412* (2013.01); *B29C 64/386* (2017.08)

(58) Field of Classification Search
CPC ........ A61F 2/2412; A61F 2/2415; A61F 2/06; G09B 23/30; G09B 23/306; B33Y 80/00; B33Y 10/00; B33Y 70/00; A61B 2034/102; A61B 2034/105; B29C 64/386
USPC .................................. 73/866.4; 434/267–275
See application file for complete search history.

(56) References Cited

U.S. PATENT DOCUMENTS

| | | | | |
|---|---|---|---|---|
| 2005/0203598 A1* | 9/2005 | Becker | ...................... | A61F 7/02 607/105 |
| 2013/0304590 A1* | 11/2013 | Motenko | ................ | G06Q 50/12 705/15 |
| 2016/0140879 A1* | 5/2016 | Hananel | ................. | G09B 23/32 434/270 |
| 2016/0325520 A1* | 11/2016 | Berger | ...................... | B32B 3/12 |
| 2016/0374431 A1* | 12/2016 | Tow | ........................ | B33Y 30/00 36/43 |
| 2018/0370125 A1* | 12/2018 | Rolland | ................ | B29C 64/245 |

* cited by examiner

*Primary Examiner* — Robert R Raevis
(74) *Attorney, Agent, or Firm* — Troutman Sanders LLP; Ryan A. Schneider

(57) ABSTRACT

Systems and methods are described herein for producing a model of a biological tissue, comprising a primary elastic material formed in the shape of an organ, and a secondary stiffener material embedded in the primary elastic material, wherein the secondary stiffener material is formed into a metamaterial design that increases the elastic modulus of the model in at least one predetermined direction. Models in accordance with embodiments mimic both the shape and mechanical properties of the organ they depict.

20 Claims, 12 Drawing Sheets
(10 of 12 Drawing Sheet(s) Filed in Color)

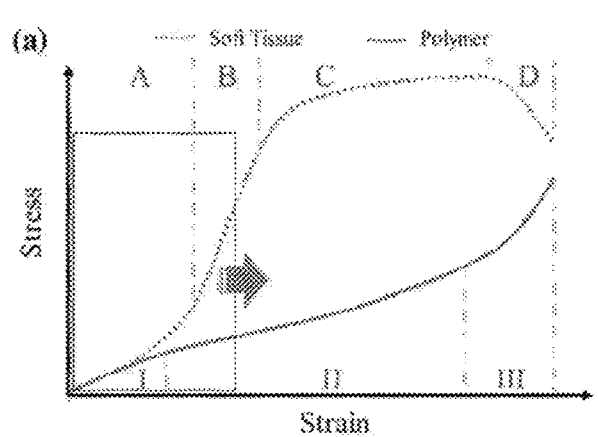
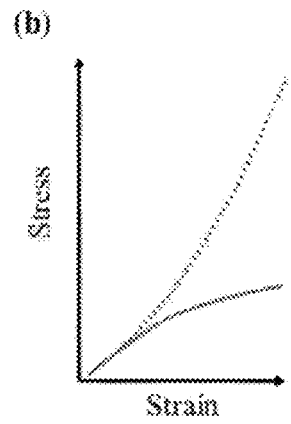
FIG. 4(a)        FIG. 4(b)
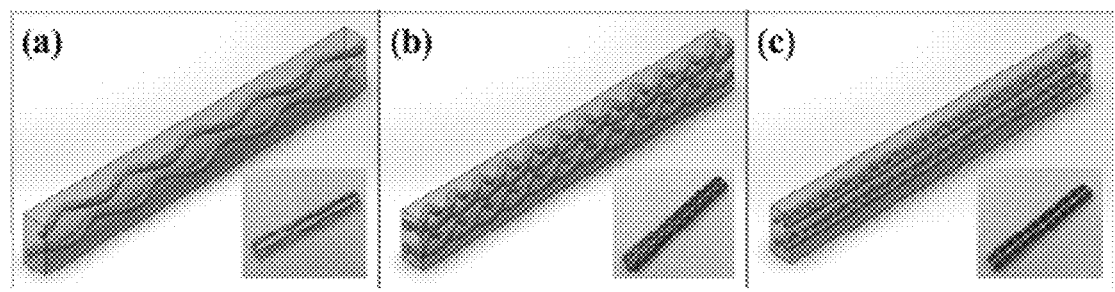
FIG. 5(a)        FIG. 5(b)        FIG. 5(c)
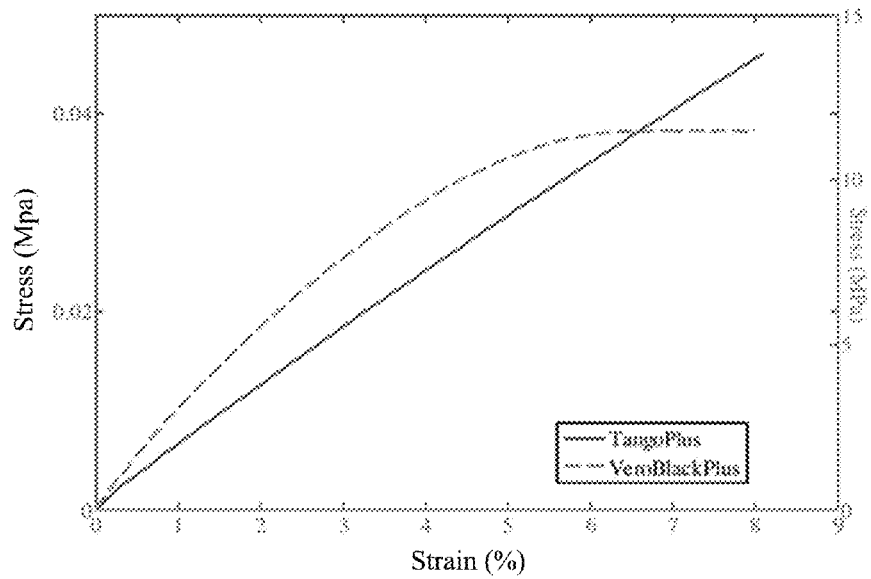
FIG. 6

3D PRINTED METAMATERIAL TISSUE-MIMICKING PHANTOMS

CROSS-REFERENCE TO RELATED APPLICATIONS

This application claims priority to U.S. Provisional Application No. 62/417,462, filed Nov. 4, 2016, the contents of which are incorporated herein by reference in their entirety.

FIELD OF INVENTION

The present disclosed technology relates to a printing technique for producing three-dimensional models of biological tissues that mimic both the shape and mechanical properties of the organs they model by using embedded metamaterials.

BACKGROUND

Transcatheter aortic valve replacement (TAVR) has emerged as a treatment option for patients with severe symptomatic aortic stenosis at high risk for surgical aortic valve replacement (SAVR). In order to select appropriate TAVR prosthesis for optimal outcome, non-invasive imaging techniques, such as CT and 3D echocardiography, are routinely performed to characterize the aortic root anatomy and ensure accurate annulus sizing. However, due to the sutureless nature of TAVR procedure, the occurrence of mild or more paravalvular leak (PVL) after TAVR is higher than after surgical aortic valve replacement (SAVR), affecting 26-67% patients. Multicenter studies have found moderate to severe post-TAVR PVL to be an independent risk factor for increased short- and long-term mortality. Although a number of PVL predictors have been proposed, there is no broad consensus on how the current practice of patient screening and prosthesis selection can be refined in order to reduce PVL.

3D printing, or additive manufacturing (AM), refers to the layer-by-layer fabrication of objects in an additive process from CAD models. It features a high ability for customization, high geometrical complexity and cost effectiveness in some cases with low production volume, which is perfectly suited for biomedical applications like prosthetics.

Although the uniaxial tensile properties of phantom materials can be close to soft tissues at small strain (<3%) range, the creep tendency, an inherent characteristic of polymers, makes them behave quite differently than the soft tissues under larger deformation. For tissue-mimicking phantoms, the strain range-of-interest is normally the working strain range of the tissue. Soft tissues typically exhibit a strain-stiffening behavior initially, which is represented by a convex stress-strain curve in the beginning. As the strain increases, the curve changes from convex to concave, which indicates yielding of the material. In contrast, the stress-strain curve of a polymer material is usually concave from the beginning, indicating a strain-softening feature. Even though the initial Young's modulus (elastic modulus) of a polymeric phantom can be designed to match the Young's modulus of the real tissue, the mechanical behavior of the phantom will deviate from the real tissue at higher strain levels.

Since creep is an intrinsic property of polymeric materials, single-material polymer 3D printing is generally not capable of generating phantoms that are mechanically accurate in the strain range-of-interest. Recent advances in 3D printed metamaterials provides new insight to this challenge.

Metamaterials were first introduced as novel electromagnetic (EM) materials and their characteristic structural length is one or more orders smaller than the EM wavelengths. Since then, the concept of metamaterials has been extended to include any materials whose effective properties are delivered by its structure rather than the bulk behavior of the base materials that composed it. In other words, the geometry, size, orientation and arrangement of the unit cells of metamaterials grant them the desired properties. Here, the value of the "metamaterial" concept is the idea of constructing artificial models of tissue with heterogeneous microstructures that, although difficult to do conventionally, can be printed using additive manufacturing.

To improve patient outcomes following TAVR procedures, an improved modeling technique is needed to better predict the interaction of the TAVR prosthesis with the human aorta, and thereby predict surgical outcomes, such as the occurrence of PVL. However, as would be understood by a person of ordinary skill in the art, the present disclosed technology is not so limited. Indeed, the techniques described herein can be applied to other biological tissues and organs, both human and animal.

SUMMARY OF THE INVENTION

Aspects of the present disclosed technology relate to a model of a biological tissue, comprising a primary elastic material formed in the shape of an organ, and a secondary stiffener material embedded in the primary elastic material, wherein the secondary stiffener material is formed into a metamaterial design that increases the elastic modulus of the model in at least one predetermined direction.

In some embodiments, the organ is an aortic valve root. In some embodiments, \ the metamaterial design is a sinusoidal wave. In some embodiments, the metamaterial design is a double helix. In some embodiments, the metamaterial design is an interlocking chain. In some embodiments, the model has a stress-strain curve that approximates the stress-strain curve of the organ.

Aspects of the present disclosed technology also relate to a method for forming a model of biological tissue, comprising creating a computer model of an organ of a patient derived from diagnostic imaging of the patient, adding a metamaterial structure within the outer surface of the computer model that increases the elastic modulus in a predetermined direction, printing a model of an organ based on the computer model of the organ with the metamaterial structure, wherein the model is printed with a primary material, and the metamaterial structures are printed in a secondary material, wherein the secondary material is harder than the primary material.

In some embodiments, the organ is an aortic valve root. In some embodiments, the diagnostic imaging is a computed tomography (CT) scan. In some embodiments, the metamaterial design is a sinusoidal wave. In some embodiments, the metamaterial design is a double helix. In some embodiments, the metamaterial design is an interlocking chain. In some embodiments, the model of Claim 1, wherein the model has a stress-strain curve that approximates the stress-strain curve of the organ the model resembles.

Aspects of the present disclosed technology also relate to a method for testing a surgical procedure, comprising creating a computer model of an organ of a patient based on diagnostic imaging of the patient; adding a metamaterial structure within the outer surface of the computer model; printing a model of an organ based on the computer model of the organ with the metamaterial structure, wherein the model is printed with a primary material, and the metamaterial structures are printed in a secondary material, wherein the secondary material is harder than the primary material inserting a prosthesis into the printed model of an organ; and evaluating the performance of the prosthesis in the model of an organ.

In some embodiments, the organ is an aortic valve root. In some embodiments, the metamaterial design is a sinusoidal wave. In some embodiments, the metamaterial design is a double helix. In some embodiments, the model has a stress-strain curve that approximates the stress-strain curve of the organ the model resembles. In some embodiments, the prosthesis is aortic valve replacement. In some embodiments, the step of evaluating the performance of the prosthesis includes circulating a fluid through the printed model, and evaluating the prosthesis for paravalvular leakage.

BRIEF DESCRIPTION OF THE FIGURES

The patent or application file contains at least one drawing executed in color. Copies of this patent application publication with color drawing(s) will be provided by the Office upon request and payment of the necessary fee.

FIG. 4($a$)-($b$) is a comparison of mechanical behaviors of soft tissue and polymer.

FIG. 5($a$)-($c$) depicts CAD models and printed samples of three metamaterials: (a) sinusoidal wave design, (b) double helix design, and (c) interlocking chain design.

FIG. 6 depicts stress-strain curves of pure TangoPlus sample (solid, left y-axis) and VeroBlackPlus sample (dashed, right y-axis).

DETAILED DESCRIPTION

Figures 1, 2:
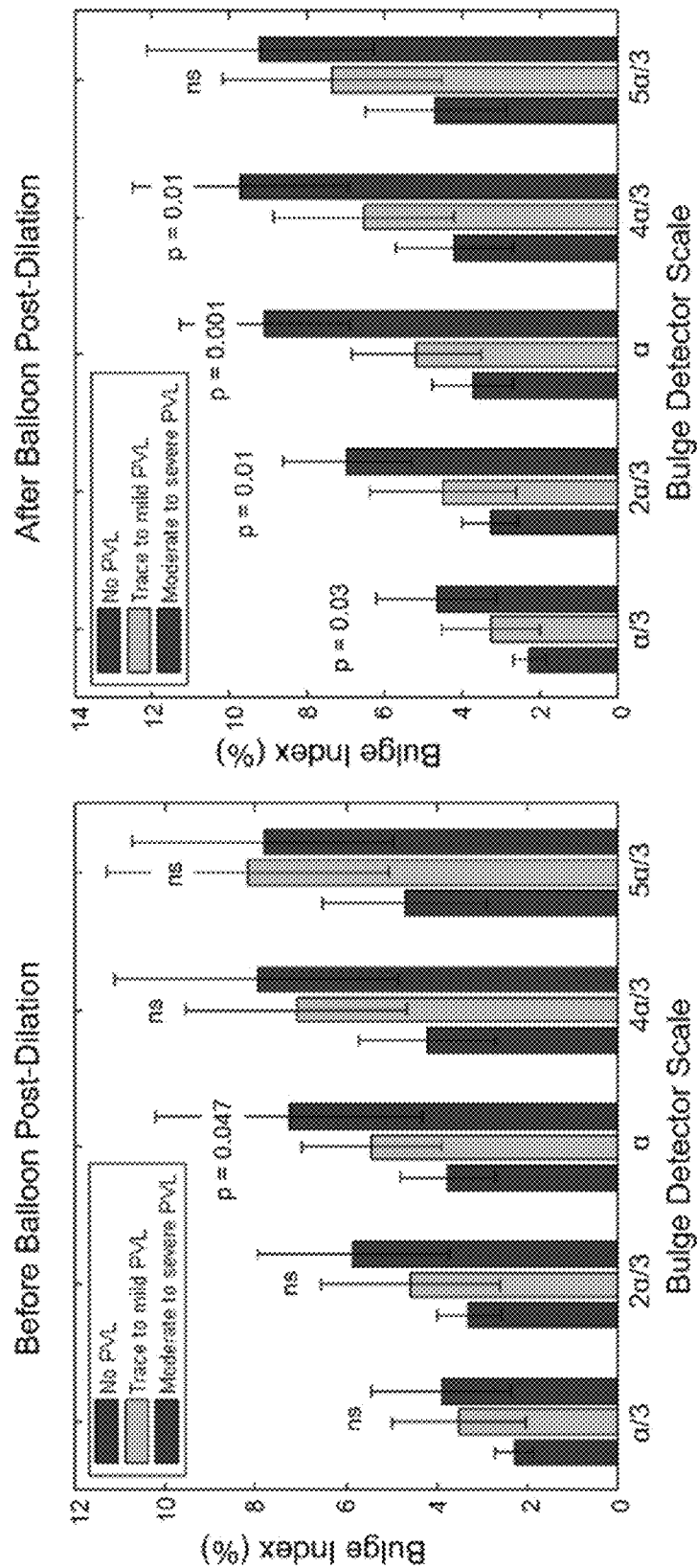
FIGS. 1-2 are a comparison of the discernibility of PVL subgroups using ANOVA based on the bulge indices calculated with variant detector scales.

The present disclosure can be understood more readily by reference to the following detailed description of example embodiments and the examples included herein. Before the example embodiments of the devices and methods according to the present disclosure are disclosed and described, it is to be understood that embodiments are not limited to those described within this disclosure. Numerous modifications and variations therein will be apparent to those skilled in the art and remain within the scope of the disclosure. It is also to be understood that the terminology used herein is for the purpose of describing specific embodiments only and is not intended to be limiting. Some embodiments of the disclosed technology will be described more fully hereinafter with reference to the accompanying drawings. This disclosed technology may, however, be embodied in many different forms and should not be construed as limited to the embodiments set forth therein.

In the following description, numerous specific details are set forth. However, it is to be understood that embodiments of the disclosed technology may be practiced without these specific details. In other instances, well-known methods, structures, and techniques have not been shown in detail in order not to obscure an understanding of this description. References to "one embodiment," "an embodiment," "example embodiment," "some embodiments," "certain embodiments," "various embodiments," etc., indicate that the embodiment(s) of the disclosed technology so described may include a particular feature, structure, or characteristic, but not every embodiment necessarily includes the particular feature, structure, or characteristic. Further, repeated use of the phrase "in one embodiment" does not necessarily refer to the same embodiment, although it may.

Unless otherwise noted, the terms used herein are to be understood according to conventional usage by those of ordinary skill in the relevant art. In addition to any definitions of terms provided below, it is to be understood that as used in the specification and in the claims, "a" or "an" can mean one or more, depending upon the context in which it is used. Throughout the specification and the claims, the following terms take at least the meanings explicitly associated herein, unless the context clearly dictates otherwise. The term "or" is intended to mean an inclusive "or." Further, the terms "a," "an," and "the" are intended to mean one or more unless specified otherwise or clear from the context to be directed to a singular form.

Unless otherwise specified, the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

By "comprising" or "containing" or "including," it is meant that at least the named compound, element, particle, or method step is present in the composition or article or method, but does not exclude the presence of other compounds, materials, particles, method steps, even if the other such compounds, material, particles, method steps have the same function as what is named.

Throughout this description, various components may be identified having specific values or parameters, however, these items are provided as example embodiments. Indeed, the example embodiments do not limit the various aspects and concepts of the disclosed technology as many comparable parameters, sizes, ranges, and/or values may be implemented. The terms "first," "second," and the like, "primary," "secondary," and the like, do not denote any order, quantity, or importance, but rather are used to distinguish one element from another.

It is noted that terms like "specifically," "preferably," "typically," "generally," and "often" are not utilized herein to limit the scope of the disclosed technology or to imply that certain features are critical, essential, or even important to the structure or function of the disclosed technology. Rather, these terms are merely intended to highlight alternative or additional features that may or may not be utilized in a particular embodiment of the disclosed technology. It is also noted that terms like "substantially" and "about" are utilized herein to represent the inherent degree of uncertainty that may be attributed to any quantitative comparison, value, measurement, or other representation. Also, in describing the example embodiments, terminology will be resorted to for the sake of clarity. It is intended that each term contemplates its broadest meaning as understood by those skilled in the art and includes all technical equivalents that operate in a similar manner to accomplish a similar purpose.

To facilitate an understanding of the principles and features of the embodiments of the present disclosure, example embodiments are explained hereinafter with reference to their implementation in an illustrative embodiment. Such illustrative embodiments are not, however, intended to be limiting.

The materials described hereinafter as making up the various elements of the embodiments of the present disclosure are intended to be illustrative and not restrictive. Many suitable materials that would perform the same or a similar function as the materials described herein are intended to be embraced within the scope of the example embodiments. Such other materials not described herein can include, but are not limited to, materials that are developed after the time of the development of the disclosed technology, for example.

A "subject" or "patient" or "individual" or "animal", as used herein, refers to humans, veterinary animals (e.g., cats, dogs, cows, horses, sheep, pigs, etc.) and experimental animal models of diseases (e.g., mice, rats). In a preferred embodiment, the subject is a human.

The term "organ" can refer to any mass of biological tissue in a patient, including entire organs, such as a heart, liver, or lungs, or any portion thereof, such as blood vessels, skin, or other anatomical structures.

The term "diagnostic imaging" can refer to CT scans, MRI images, X-Rays, Ultrasounds, or any other technique for observing the structure of an anatomical feature, as would be understood by a person of ordinary skill in the art.

Three-dimensional (3D) printing is a fast and cost-effective way to accurately reproduce patient-specific anatomies for education, training and pre-procedural planning. Multimaterial printing using colorful soft and rigid materials can create realistic visual and tactile experiences. Described herein is a novel metamaterial printing technique to produce models with nonlinear and anisotropic mechanical properties, which were comparable to biological tissues. In some embodiments, the present disclosed technology can be used to produce models of the aortic root. However, the disclosed technology is not so limited, and can be used to produce models of a wide array of biological tissues, such as blood vessels, lungs, and other organs.

Embodiments of the present disclosed technology provide a model of a biological tissue, comprising a primary elastic material formed in the shape of an organ, and a secondary stiffener material embedded in the primary elastic material, wherein the secondary stiffener material is formed into a metamaterial design that increases the elastic modulus of the model in at least one predetermined direction. The metamaterial design can comprise a sinusoidal wave, a double helix, or an interlocking chain. As would be understood by a person of ordinary skill in the art, other metamaterial designs could be used, such that the embedded secondary stiffener material provides the appropriate mechanical property to the model of an organ.

Embodiments of the present disclosed technology can be fabricated from a 3-D computer model of the organ of a patient. The 3-D computer model can be obtained from diagnostic imaging, such as a CT scan or MRI image, among others. As would be recognized by a person of ordinary skill in the art, the 3-D computer model could be obtained from any source, or even modeled manually based on observations.

A 3-D model in accordance with an embodiment can be modified prior to printing, such as, for example, to design around printer limitations, such as printer material shrinkage, or for providing a more accurate mechanical model at the expense of geometric accuracy. In some embodiments, the outside walls can be thinned or thickened, as the case may be.

Embodiments of the present disclosed technology can comprise a model printed using a multi-material 3-D printer. In some embodiments, the primary soft material and the embedded stiffened material can be printed in the same pass. In some embodiments, the stiffness of the primary soft material or embedded stiffened material can be tuned by mixing multiple materials to form the model or embedded stiffened material.

Embodiments of the present disclosed technology can comprise a model of an aortic valve root. However, as would be understood by a person of ordinary skill in the art, other organs could be so modeled. For example, adult human lungs or livers could also be modeled. In addition, the mechanical properties of the parts of an adult human cardiovascular system vary greatly from that of a newborn or juvenile cardiovascular system. Models that accurately model the shape and mechanical properties of these alternative body systems are within the scope of the disclosed technology.

Embodiments of the present disclosed technology can be used for pre-operative planning. For example, for TAVR procedures, a model of an aortic root can be produced that models the mechanical properties of the aortic root of a particular patient. A replacement valve prosthesis can be inserted into the model, and tests conducted to determine prosthesis performance. A detailed example of such an application is provided herein. However, as would be understood by a person having ordinary skill in the art, a variety of other pre-operative planning tasks can be accomplished using a model in accordance with an embodiment. For example, a surgeon can use a model in accordance with an embodiment to choose between surgical techniques, select an appropriate prosthesis, or use the model to explain the procedure to colleagues or the patient.

In one embodiment, models in accordance with an embodiment can be used to model aortic roots for pre-operative evaluation of the likelihood of PVL in TAVR patients. Balloon post-dilation of the prosthesis is often performed post-deployment in patients who had significant PVL after the initial valve deployment. Whether this fixes the PVL can be hard to predict, and the mechanism of such a fix was not fully understood. Undersizing of the prosthesis has been identified as a major cause of PVL. However, in this study, a lower annular strain which would be seen with undersizing, was not necessarily associated with the presence of or the degree of PVL. This may be due to the fact that in all of these cases annulus sizing was done by standard pre-procedural imaging. Instead, the bulge index, which can be a measure of annular unevenness (areas of low-high-low strain pattern), was predictive of PVL both immediately after deployment (pre-balloon) and post-balloon. However, pre-balloon the annular calcium volume was also predictive of the degree of PVL, and was a better predictor of mild PVL versus moderate PVL (AUC 83% vs 77%, respectively). In the post-balloon-dilation setting, annular calcium volume was not predictive of the degree of PVL while bulge index was. Furthermore, the annular calcium volume was inferior to bulge index in predicting ≥mild PVL versus moderate PVL (AUC 75% vs 95%, respectively). Therefore, balloon dilation likely worked as a fine-tuning tool that optimized the contact between the prosthesis and the aortic root, and thus improved the global sealing of the annulus.

Furthermore, a bulge detector scale that equaled the inter-strut angle of the CoreValve at the LVOT end (24° for valve sizes 26 mm, and 30° for 23 mm valve size) performed the best with regard to the prediction of moderate PVL (FIGS. 1 and 2) before and after balloon dilation. On the contrary, smaller and larger scale bulge detectors were not as good for predicting significant PVL. Perhaps the random distribution of the severity and location of annular calcium, which creates various scales of annular strain unevenness, results in imperfect annular sealing and significant PVL. Balloon dilation likely smoothed out these areas of large annular unevenness in a global fashion. However, it may not as effectively fix focal PVL that can be caused by small scale of strain unevenness that extends between two consecutive struts. Thus, calcium volume was superior to the bulge detector pre-balloon to predict significant PVL. However, if the bulge persists between two consecutive struts even after balloon dilation, then there can be significant residual PVL. This hypothesis is exemplified by Patient #5 in FIG. 3 where the pre-balloon PVL was located at 12 o'clock (see supplement) within an area of large annular strain but with an angular extent that was larger than 24° and, hence, was not seen as a hot area in the bulge index map. This PVL disappeared post-balloon as we would expect from the hypothesis that the balloon dilation evens out large bulge areas. Additionally, the final residual mild PVL was now located at 5 and 7 o'clock positions at the sites of the bulges extending between two consecutive struts at an angular extent of 24°.

Annular calcification in TAVR was an important risk factor of PVL, but not all incidents of them actually lead to PVL. For the prediction of moderate PVL after balloon dilation, the specificity of annular calcification was only 50%, while the specificity of the bulge index was 79%. If valve sizing and deployment is optimal, then the amount of annular calcification can be a necessary but not sufficient condition for the occurrence of PVL. Instead, the shape, size, and location of the annular calcification may be instrumental in causing focal uneven strain distribution (high bulge index) resulting in significant PVL. The 3D printed phantom provides a practical in vitro way to quantitatively assess the distribution of post-TAVR annular strain. This may lead to a better understanding of the role of the annular calcification in the genesis of PVL post-TAVR, and may be extendable to other transcatheter valve therapies.

A novel indicator of the post-TAVR annular strain unevenness, the annular bulge index, quantified by in vitro TAVR simulation on a patient-specific 3D printed phantom, using unique tissue-mimicking metamaterials, outperformed established variables and achieved high accuracy in predicting the occurrence, severity, and location of post-TAVR PVL. Thus, it may be feasible to perform procedural simulations on a 3D printed tissue-mimicking phantom to gather relevant pathophysiological information for pre-TAVR planning among certain high-risk patient populations. Such information may refine the current techniques for screening patients and the selection of the TAVR prosthesis, and potentially reduce the rate of PVL.

Design of Metamaterial Samples

The passive biomechanical properties of human soft tissues were determined by the microstructure of the tissues and extracellular matrix (ECM) at the cellular level and how those structures organize and interact at higher levels. For instance, the nonlinear behavior of human vessels comes from the wavy collagen fibers in the proteoglycans, which can be a major component of the ECM, being straightened under tensile loading (271, 124 We imitated this observation by embedding wavy stiff structures into soft polymeric matrix. Ideally, those stiff structures will straighten up during elongation and compensate for the creep of the matrix polymer. Three types of metamaterial samples were designed using Solid-Works (Dassault Systems SOLID-WORKS Corp.): those containing sinusoidal wave (SW) fibers, double helix (DH) fibers, and interlocking chains (IC), respectively. The CAD models and pictures of printed samples are demonstrated in FIGS. 5(a)-(c). FIG. 5(a) is the sinusoidal wave sample, FIG. 5(b) is the double-helix sample, and FIG. 5(c) is the interlocking chain sample. The SW design has often been used as an assumption for theoretical analysis or numerical simulation of natural wavy fibrous systems. The wavelength, X, and amplitude, A. of the sinusoidal wave could serve as design parameters for property tuning. The DH design resembles the microstructure of filament actin (F-actin) strands. The tuning parameters for the double helix design are the radius of the helix, rh, and the pitch, h. The IC design was an attempt at achieving nonlinearity by non-continuous fiber structure, even though there can be no such structural design observed in ECM. Its tuning parameters include distance between two links, d, and chain width, w. All samples shared one tuning parameter, which can be the radius of fibers, rl. Each sample model was assembled from a soft matrix part file and a stiff reinforcing microstructure. Dimensions of all samples were 30 mm in length and 4 mm in width to accommodate dimension requirements of uniaxial tensile tests. The thickness of all samples were 2 mm and each repetitive stiff structure inside the samples were 2 mm apart along the width direction.

Table 1 summarizes the design parameters of the samples prepared for mechanical testing. For each parameter setting, three replicates were fabricated.

TABLE 1

Samples fabricated for tensile tests.

| Sample ID | Sample Type | Design Parameters (mm) |
|---|---|---|
| SW1 | Sinusoidal Wave | $\lambda = 10$, $A = 0.6$, $r_f = 0.3$ |
| DH1 | Double Helix | $r_h = 0.6$, $h = 5$, $r_f = 0.2$ |
| IC1 | Interlocking Chain | $d = 5$, $w = 1$, $r_f = 0.15$ |

Materials, Equipment, and Testing Protocols

The metamaterial samples were fabricated on a Connex350® 3D printer (Stratasys Ltd). The layer thickness of printed part is 30 μm, and the in-plane accuracy is 0.1 mm. The base materials used for stiff fiber and elastic matrix are VeroBlackPlus® (RGD875) and TangoPlus® (FullCure 930), respectively. These two materials represent the two extremes of printable materials with VeroBlackPlus being the stiffest and TangoPlus the most elastic. The Connex350 can also mix those two base materials at a certain ratio and print them simultaneously to form digital materials that have mechanical properties between the base materials. In the present example only the base materials were used to prepare the samples, but in some embodiments, material choice may also serve as a tuning factor. Uniaxial tensile tests were conducted using Q800 Dynamic Mechanical Analysis (DMA) (TA Instruments) under controlled strain mode at room temperature for all samples except those made of pure VeroBlackPlus, which were tested using RSA III DMA (TA Instruments) due to the large Young's modulus. The strain rate was set to a small value of 1%/min to achieve a quasi-static process. The maximum strain was set to 8% because the interface between VeroBlackPlus and TangoPlus starts to break down around a strain level of 9%. Testing data was analyzed using TA Universal Analysis software.

Stress-Strain Curves of Base Materials

Although the basic mechanical properties of VeroBlackPlus and TangoPlus are provided by Stratasys, the elastic moduli are represented by widely ranged values at unknown strain levels. In addition, the actual properties of the materials in printed part largely depend on the parameter settings of the printer and how the parts are built. In order to find out the actual mechanical properties of the materials in the samples, we fabricated a pure VeroBlackPlus sample and a pure TangoPlus sample with the same dimension and part orientation as the meta materials samples. The single-material samples were tested following the same testing protocol described above, and the results are shown in FIGS. 4(a) and 4(b). Those curves were used to define the non-linearity of the base materials in the FEA simulations using the Multi-linear Kinematic Hardening model.

Finite Element Analysis was conducted in addition to the actual tensile tests to provide quick insights on how the design parameters would affect the mechanical properties. ANSYS® (R15.0) was used as the simulation software. The CAD models were imported into ANSYS in the LES format and quadratic tetrahedral elements were used for meshing. For each design, only one periodic unit along the length direction was used in the simulations for computational efficiency. FIG. 7(a)-(d) demonstrates the model and meshing for the FEA simulations using the DH design as an example. The number of total nodes in each model is in the range of 35,000-50,000 depending on the geometrical complexity. To calculate the stress-strain curve, one end of the model was fixed in x, y and z directions while a series of strain levels up to 8% along the x direction were applied to the other end. FIG. 8 demonstrates how the wavy fibers in the SW design are gradually straightened and carries more load as the strain level increases. To investigate the effects of design parameters on the mechanical behavior of the metamaterials, different variants of the SW design were simulated. Table 2 lists all the designs used in simulation.

TABLE 2

Samples designed for computational simulation

| Sample ID | Sample Type | Design Parameters (mm) |
|---|---|---|
| SW1 | Sinusoidal Wave | $\lambda = 10$, $A = 0.6$, $r_f = 0.3$ |
| SW2 | Sinusoidal Wave | $\lambda = 10$, $A = 0.6$, $r_f = 0.3$ |
| SW3 | Sinusoidal Wave | $\lambda = 10$, $A = 0.6$, $r_f = 0.3$ |
| SW4 | Sinusoidal Wave | $\lambda = 10$, $A = 0.6$, $r_f = 0.3$ |
| DH1 | Double Helix | $r_h = 0.6$, $h = 5$, $r_f = 0.2$ |
| IC1 | Interlocking Chain | $d = 5$, $w = 1$, $r_f = 0.15$ |

The SW Design

Figure 9:
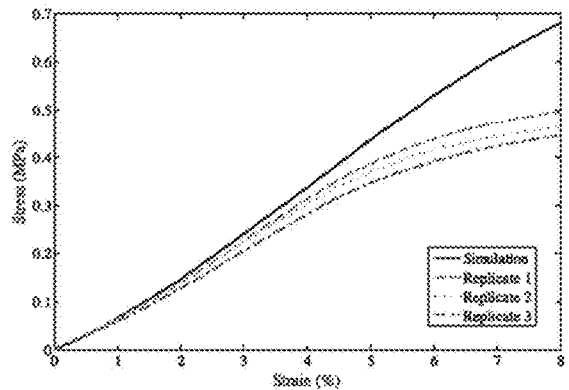
FIG. 9 depicts stress-strain curves from uniaxial tensile tests of 3 replicates and simulation of SW1.

The results from the uniaxial tensile tests of three replicates of SW1 are plotted with the simulation results of SW1 in FIG. 9. The experimental results follow the same trend of the simulation but deviate from the simulation as the strain increases. The larger discrepancy at higher strain levels can be explained by the defects in the printed samples and the imperfect interface between the stiff fibers and the soft matrix. Both simulation and experimental results show a concavity change. The inflection point, where the stress-strain curve changes from convex to concave, can be determined mathematically by finding the point where the second derivative of the curve changes sign. In this case, it is easy to see that the first derivative of the curve. Young's modulus, achieves its maximum at the inflection point. The initial modulus (E0), the maximum modulus (E1), the strain at the inflection point (si), and the modulus at 8% strain (E0•08) were the specifications used to characterize a stress strain curve in this study. For the SW1 design, the results are listed in Table 3.

TABLE 3

Stress-strain curve specifications of the SW1 samples and simulation

|  | $E_0$(MPa) | $E_i$(MPa) | $\varepsilon_i$(%) | $E_{0.08}$ (MPa) |
|---|---|---|---|---|
| Replicate 1 | 6.054 | 10.170 | 3.77 | 1.557 |
| Replicate 2 | 6.165 | 9.461 | 3.89 | 1.092 |
| Replicate 3 | 5.415 | 8.884 | 4.19 | 1.102 |
| Simulation | 6.105 | 10.104 | 4.83 | 6.731 |

The results indicated that all three SW1 samples exhibited strain-stiffening behavior up to around 4% strain, which can never be achieved by a single polymeric material. The value of $\varepsilon i$ is close to the experimental result of collagen-rich tissues, such as the sole tendon. However, $E_0$, $E_i$, and $E_{0.08}$ of the printed samples are one magnitude lower than the values of those collagen-rich tissues. Comparing to the elastin-rich tissues, such as the nuchal ligament, the printed samples have a very low $\varepsilon i$ and high moduli. Now that the nonlinear trend can be mimicked by the printed metamaterials, those values could be achievable with proper selection of base materials and design parameters.

The DH Design

Figure 10:
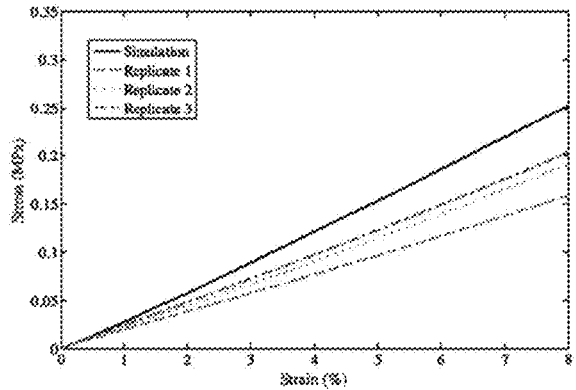
FIG. 10 depicts stress-strain curves from uniaxial tensile tests of 3 replicates and simulation of DH1.

The stress-strain curves of DH1 are plotted in FIG. 10 and the curve specifications are listed in Table 4. The concavity check of the curves indicates that all curves up to 8% strain are slightly convex. Assuming the materials will hit the yielding point eventually and the curves will become concave afterwards, there should be an infection point somewhere beyond 8% strain. The moduli of DH2 samples are smaller than the SW1 samples. These results implied that the DH design could potentially be used to mimic the elastin rich tissues which have yielding strain from 15% to 50% and small moduli below 1 MPa [29].

TABLE 4

Stress-strain curve specifications of the DH1 samples and simulation

|  | $E_0$(MPa) | $E_i$(MPa) | $\varepsilon_i$(%) | $E_{0.08}$ (MPa) |
|---|---|---|---|---|
| Replicate 1 | 1.982 | >2.069 | >8 | 2.069 |
| Replicate 2 | 2.236 | >2.556 | >8 | 2.556 |
| Replicate 3 | 2.469 | >2.680 | >8 | 2.680 |
| Simulation | 2.704 | >3.359 | >8 | 3.359 |

The IC Design

Figure 11:
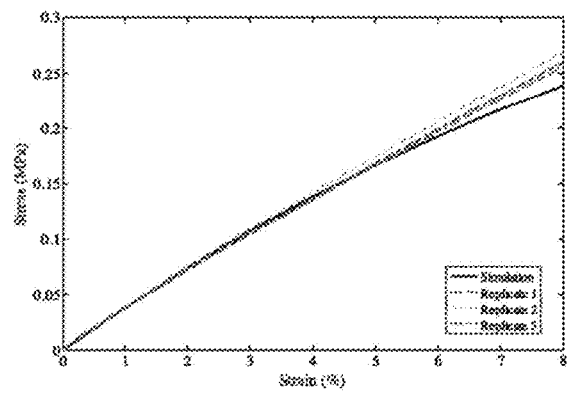
FIG. 11 depicts stress-strain curves from uniaxial tensile tests of 3 replicates and simulation of ICI.

The stress-strain curves of IC1 are plotted in FIG. 11 and the curve specifications are listed in Table 5. The stress-strain curves are concave for both the simulation and experimental data. This result is not surprising since it is not derived from any microstructure observed in natural ECM. Although the IC design did not demonstrate the desired strain-stiffening feature, we report the results here as others may find the results interesting.

TABLE 5

Stress-strain curve specifications of the IC1 samples and simulation

|  | $E_0$(MPa) | $E_i$(MPa) | $\varepsilon_i$(%) | $E_{0.08}$ (MPa) |
|---|---|---|---|---|
| Replicate 1 | 5.688 | — | — | 3.065 |
| Replicate 2 | 4.867 | — | — | 3.060 |
| Replicate 3 | 4.464 | — | — | 2.838 |
| Simulation | 3.867 | — | — | 2.185 |

Effects of Design Parameters

Figure 12:
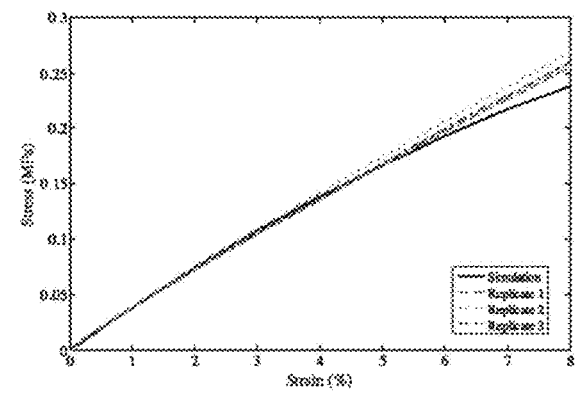
FIG. 12 depicts stress-strain curves of the four variants of the SW design.

Curves plotting the mechanical behavior of printed metamaterials using FEA simulations for all four variants of the SW design are depicted in FIG. 12 and the specifications are listed in Table 6.

TABLE 6

Stress-strain curve specifications of the IC1 samples and simulation

|  | $E_0$(MPa) | $E_i$(MPa) | $\varepsilon_i$(%) | $E_{0.08}$ (MPa) |
|---|---|---|---|---|
| SW1 | 6.105 | 10.104 | 4.83 | 6.731 |
| SW2 | 5.008 | 7.853 | 5.62 | 6.806 |
| SW3 | 8.579 | 11.348 | 2.91 | 4.783 |
| SW4 | 2.809 | 3.598 | 2.66 | 1.274 |

The results indicate that the mechanical behavior of printed metamaterials is heavily affected by the design parameters. Each design parameter affects all four specifications of the stress-strain curve. Most importantly, the design parameters affect the specifications in different ways. For example, a decrease in will cause lower E0 and higher $\varepsilon i$, while a decrease in rf will cause both E0 and $\varepsilon i$ to decrease. This means one can achieve desired E0 and $\varepsilon i$ with a proper combination of and rf. Other specifications of the stress-strain curve can be tuned the same way. The shape of fibers can be designed as combination of multiple sinusoidal waves, which will introduce more design parameters into the microstructure of printed metamaterials. In addition to the microstructure, the mechanical properties of the base materials for the fibers and matrix can also serve as tuning parameters. Although a proper design tool needs to be developed for this purpose, the 3D printing of mechanically accurate tissue-mimicking phantom is proven to be feasible with this study.

Example

We hypothesized that the uneven distribution of strain in the annulus during TAVR contributed to the occurrence of PVL, and this could be quantitatively assessed using the 3D printed phantom in vitro. This was a retrospective, single-center, observational study approved by the Institutional Review Board of Piedmont Healthcare. We included 22 patients who underwent clinically-indicated TAVR with a self-expandable Medtronic CoreValve system between April 2014 and September 2015, and constituted a representative spectrum of different degrees of post-TAVR PVL. In order to reduce operator-induced variability in the TAVR simulation, we did not include patients who received balloon-expandable valves in this study. Prior to the TAVR procedure, all patients received a contrast-enhanced cardiac CT scan. Prosthesis size was determined by the CT-derived annulus diameter as per standard recommendations. During the TAVR procedure, valve implantation was performed under the guidance of fluoroscopy and transesophageal echocardiogram (TEE). Four patients out of the 22 were excluded from the study. Two of the excluded patients had predominant sub-annular deployment of the first valve requiring a second prosthesis (valve-in-valve); and two others had damage to the 3D printed phantoms due to technical issues. The initial positioning and anchoring of the CoreValve system was optimal and successful in the remaining 18 patients. However, TEE revealed seven patients had moderate to severe PVL immediately after the initial valve deployment, which required post-deployment balloon dilation to reduce PVL. TEE post balloon dilation showed the PVL in three of these patients were reduced to trace or mild, and in the other four the PVL degrees remained unchanged.

The pre-procedural contrast-enhanced CT scan was performed with a 320-detector row CT scanner (Aquillion ONE, Toshiba Medical Systems, Otawara, Japan), using an institutional TAVR CT protocol. Annulus diameter was measured at the phase of peak aortic opening. Annular ellipticity was calculated by dividing the maximum diameter by the minimum diameter. Total and regional calcium volumes were quantified in the aortic root, the left ventricular outflow tract (LVOT), and the annular region, using an attenuation thresholding method as described in Khalique O K., Hahn R T., Hemal G., et al. *Quantity and Location of Aortic Valve Complex Calcification Predicts Severity and Location of Paravalvular Regurgitation and Frequency of Post-Dilation After Balloon-Expandable Transcatheter Aortic Valve Replacement*. JACC Cardiovasc Intery 2014; 7:885-94.

PVL was evaluated by TEE during and immediately after the TAVR procedure, based on the VARC-2 recommendations and the unifying grading scheme proposal, and was graded as none, trace, mild, moderate, or severe. See Kappetein A P, Head S J, Genereux P, et al. *Updated standardized endpoint definitions for transcatheter aortic valve replacement: the Valve Academic Research Consortium-2 consensus document*. Eur J Cardiothorac Surg 2013; 145: 6-23.

Figure 13:
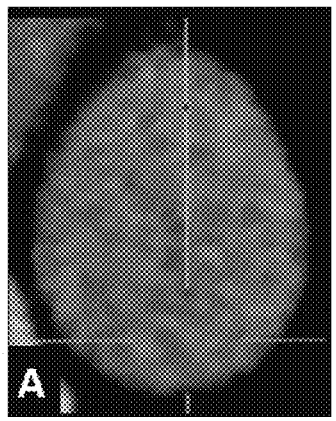
FIGS. 13-15 depict a CT cross-sectional views at the ascending aorta and the valsalva, and the longitudinal view, respectively.
Figure 14:
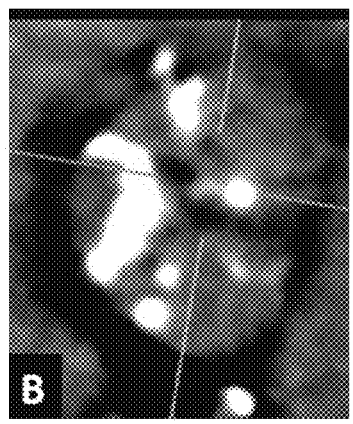
Figure 15:
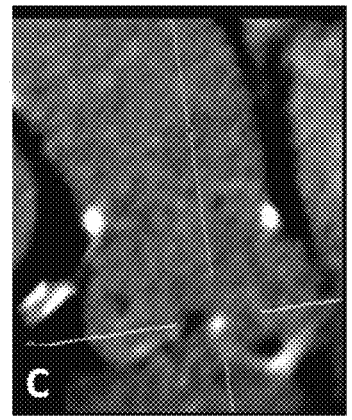
Figure 16:
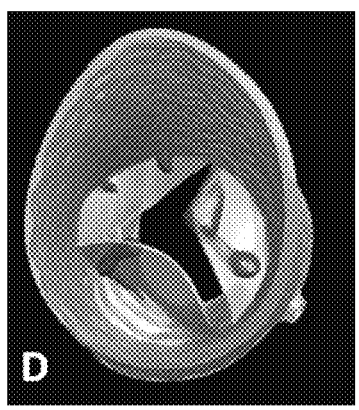
FIGS. 16-18 are the 3D computational model viewing from the ascending aorta, the left ventricular outflow tract, and the side.
Figure 17:
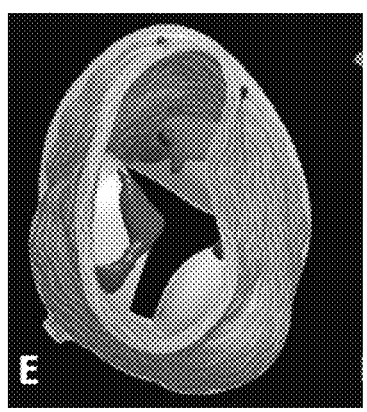
Figure 18:
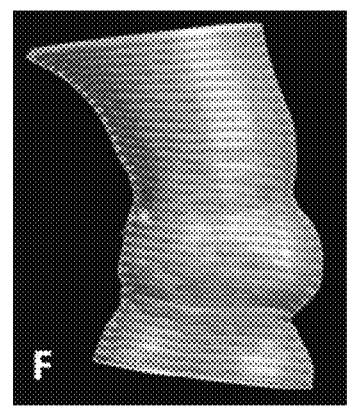
Figure 19:
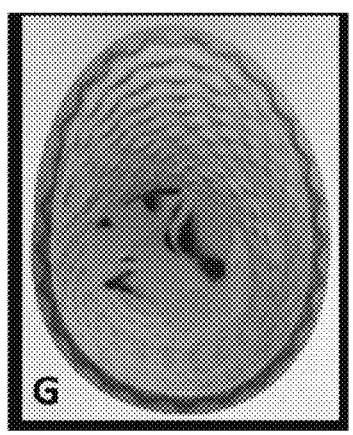
FIGS. 19-21 are the 3D printed phantom viewing from the ascending aorta, the left ventricular outflow tract, and the side. The calcifications and the fibers were printed with black materials for better illustration.
Figure 20:
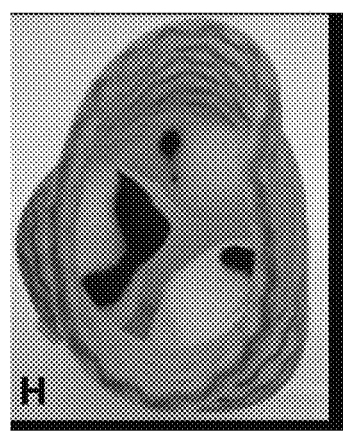
Figure 21:
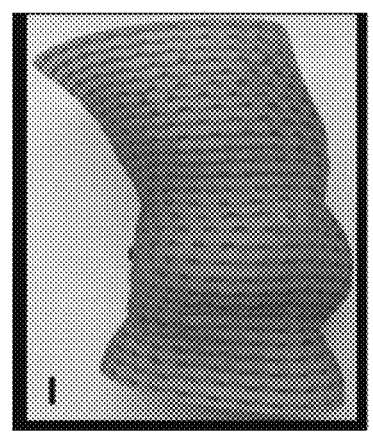

FIGS. 13-15 show pre-TAVR CT images taken at peak aortic valve opening that were identified and used to produce the 3D model of the aortic root. Research software (CT Auto Valve, Siemens Corporate Technology, Princeton, N.J.) was used to semi-automatically segment the images and produce a single-layer 3D model of the aortic root, which consisted of the arterial wall, the LVOT, and the valvular leaflets. As shown in FIG. 16-18, software was used to refine the 3D model and empirically add a 2.0-mm wall thickness to the aortic root and a 0.5-mm thickness to the leaflets. In addition, calcified lesions were extracted based on attenuation thresholding and converted into a 3D mesh model. Based on the metamaterial configurations, sinusoidal fibers were created and embedded in the 3D model of the aortic wall to achieve strain-stiffening properties comparable to human aortic tissues. Finally, the 3D models of the aortic root, the leaflets, the calcified lesions, and the fibers were converted into the Stereolithography (STL) format, and exported to a multi-material 3D printer (Stratasys PolyJet Connex 350, Eden Prairie, Minn.) for printing. TangoPlus, VeroWhitePlus, and a digital material RGD8525 were used to print the aortic root soft tissues, the calcified lesions, and the embedded fibers, respectively (FIGS. 19-21).

Figure 22:
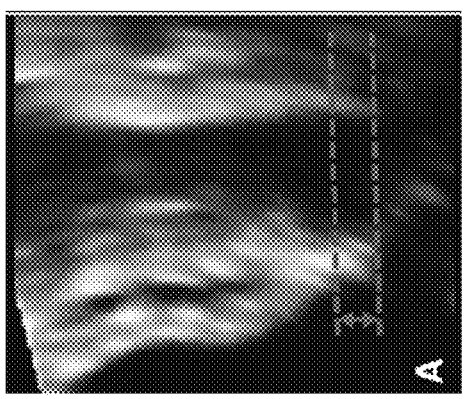
FIG. 22 shows the clinical intraprocedural trans-esophageal echocardiogram.
Figure 23:
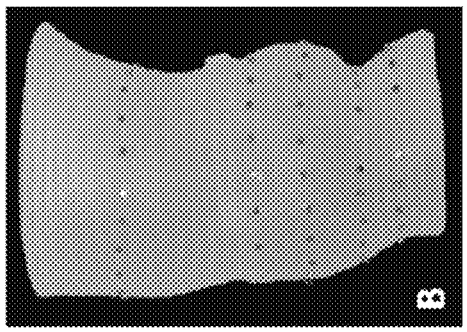
FIG. 23 is the 3D printed phantom with the radiopaque landmarks.
Figure 24:
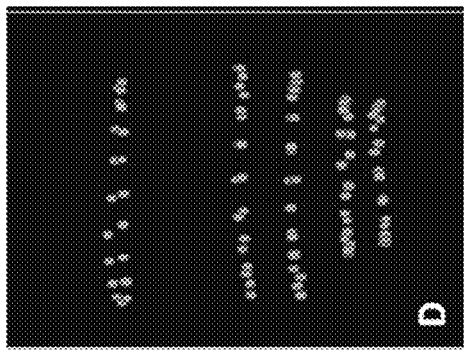
FIG. 24 is a 3D reconstruction of a CT scan of the 3D printed phantom with radiopaque landmarks of FIG. 23.
Figure 25:
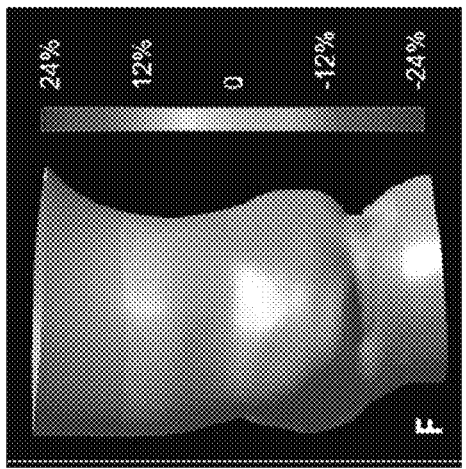
FIG. 25 is a computer model depicting the strain distribution within the aortic root with an implanted prosthesis.
Figure 26:
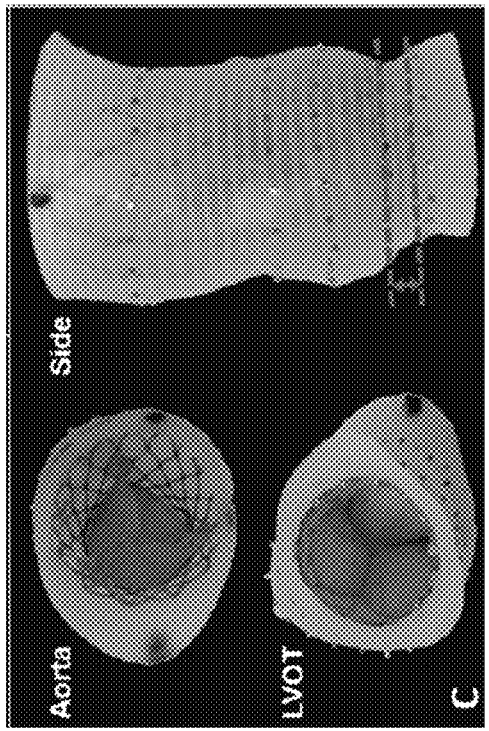
FIG. 26 shows the phantom implanted with the prosthesis, viewing from the aorta, the LVOT, and the side.
Figure 27:
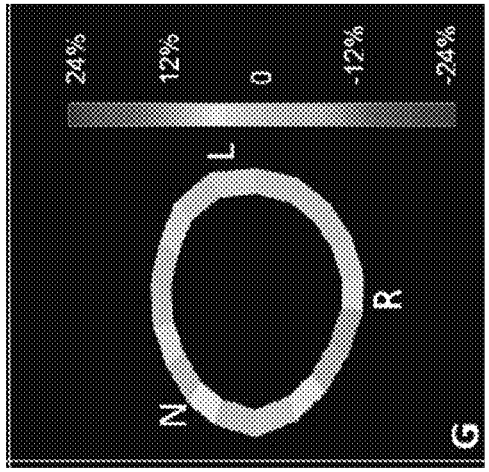
FIG. 27 is a 3D reconstruction of a CT scan of the 3D printed phantom with an implanted prosthesis of FIG. 26.
Figure 28:
FIG. 28 is the strain distribution of the aortic annulus of the model shown in FIG. 26.

For each patient, according to the size and model used in the clinical procedure, the same self-expandable CoreValve prosthesis was selected and manually implanted in the 3D printed phantom in vitro. FIGS. 22-28 illustrate the use of the physical model to estimate aortic root stress. FIG. 22 shows the clinical intraprocedural trans-esophageal echocardiogram. FIG. 23 is the 3D printed phantom with the radiopaque landmarks. FIG. 24 is a 3D reconstruction of a CT scan of the 3D printed phantom with radiopaque landmarks of FIG. 23. FIG. 25 is a computer model depicting the strain distribution within the aortic root with an implanted prosthesis. FIG. 26 shows the phantom implanted with the prosthesis, viewing from the aorta, the LVOT, and the side. FIG. 27 is a 3D reconstruction of a CT scan of the 3D printed phantom with an implanted prosthesis of FIG. 26. FIG. 28 is the strain distribution of the aortic annulus of the model shown in FIG. 26.

During the implantation, the prosthetic valve was carefully deployed to the same depth as in the clinical procedure. The prosthesis was carefully adjusted in the phantom to ensure optimal orientation and apposition. Because the CoreValve prosthetic valve is a shape memory device made of nitinol, the phantom and the implanted prosthesis were submerged in 37° C. water to ensure the full expansion of the valve as in the in vivo environment.

To quantify the aortic root strain distribution after the TAVR implantation in the 3D printed phantom, as shown in FIGS. 23-24 and 27, small radiopaque beads were attached to the surface of the phantom circumferentially at the levels of the LVOT, the annulus, the center of the sinus of valsalva, the sinotubular junction, and the ascending aorta, to serve as landmark points. The aortic root phantom underwent CT scans before and after the in-vitro TAVR implantation, using a modified CT calcium scoring protocol. By detecting and tracking the landmark points, the circumferential strains in the aortic root can be calculated by projecting the derivatives of the landmarks' displacements to the circumferential direction. As shown in FIG. 24-25, circumferential strains were quantified at the five levels, and the whole aortic root strain distribution was obtained via interpolation. At the annular level, maximum, mean, and minimum strain values were calculated in each phantom.

Figure 31:
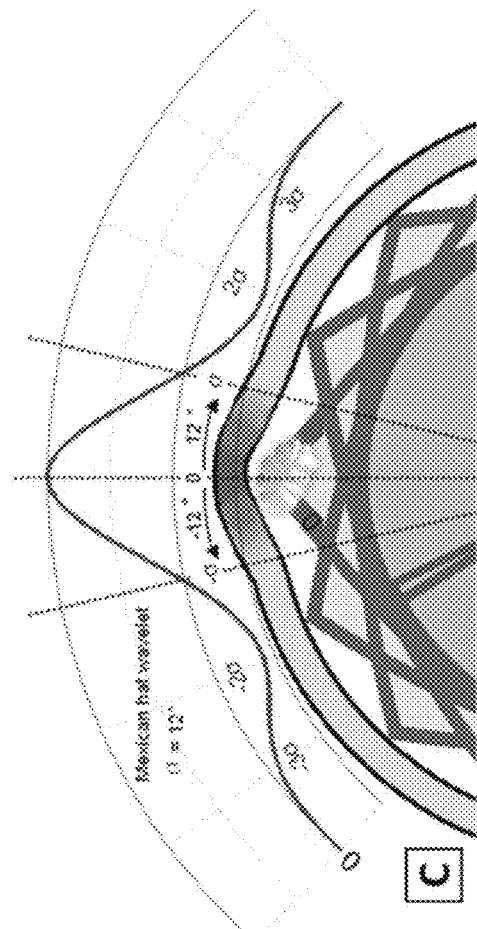
FIG. 31 shows the design of the bulge detector.
Figure 33:
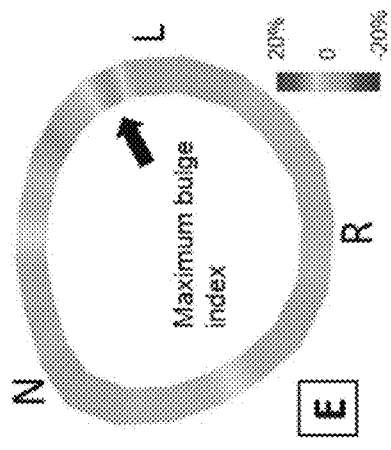
FIGS. 32 and 33 are the resulting annular strain and bulge index maps, respectively.
Figure 32:
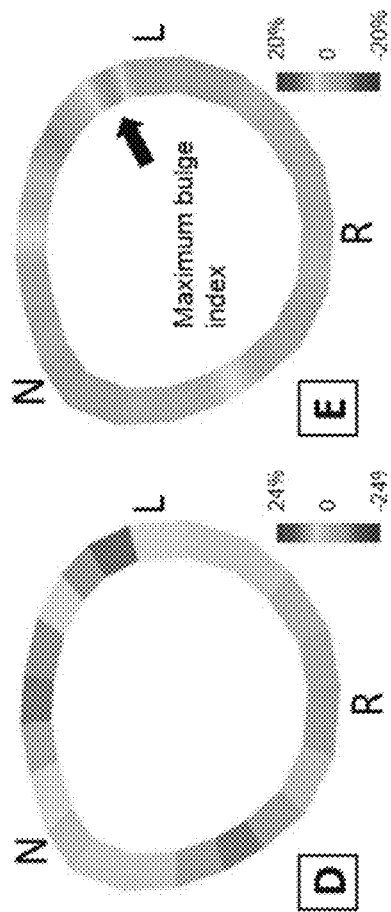
Figure 29:
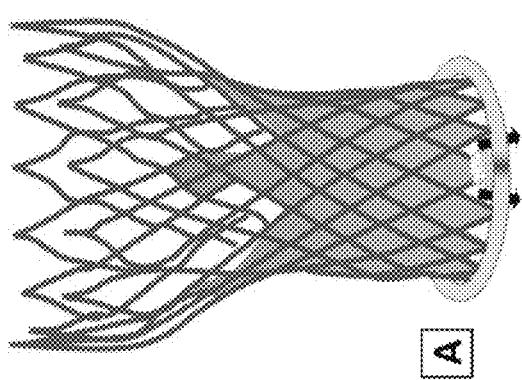
FIGS. 29 and 30 illustrate the hypothesis of PVL mechanism.
Figure 30:
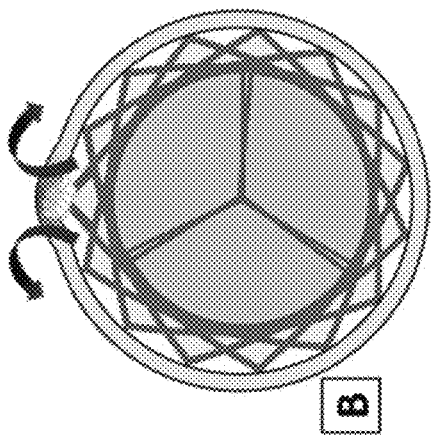

FIGS. 29-33 illustrate the deployment of a replacement valve in an aortic root, and the measurement of bulge along the perimeter of the aortic root. FIGS. 29 and 30 illustrate the hypothesis of PVL mechanism. FIG. 31 shows the design of the bulge detector. FIGS. 32 and 33 are the resulting annular strain and bulge index maps, respectively.

Based on the design of the CoreValve prosthesis, which had 12 or 15 struts at the ventricular end (The CoreValve 23 mm has 12 struts, and all the other sized valves have 15 struts), we designed a bulge detector using a Mexican hat wavelet, to detect the low-high-low strain pattern along the phantom's annulus after the in vitro implantation. The width of the wavelet's positive peak was set to equal to the circular angle between two neighboring struts of the CoreValve. The bulge index was calculated by convolving the annular strain with the detector, and in each phantom, the maximum bulge index was reported. In addition, to assess the effect of varying the detector scale, bulge detectors with different widths were also tested.

Continuous variables were reported as mean±SD. Statistical significance was defined as p<0.05. Patients were divided into three subgroups based on the TEE indicated PVL degrees immediately after the deployment of the prosthetic valve and after the balloon post-dilation. The subgroups were defined as I. no PVL, 2, trace-mild PVL, and 3. moderate-severe PVL. One-way analysis of variance (ANOVA) and Kruskal-Wallis test were used to test the difference between the subgroups, when Levene's test was negative and positive, respectively, T-test and receiver-operating characteristic (ROC) analysis were performed using ≥moderate PVL as classification variable. The area under the ROC curve (AUC) was calculated, and the cutoff value was determined by searching for the highest combination of sensitivity and specificity on the ROC curve. Multiple logistic regression using the stepwise method (entering and removal criteria were p<0.05 and p>0.1, respectively) was performed to determine independent predictors of ≥moderate PVL. Statistical analysis was performed using Medcalc (v16.4.3 Medcalc Software bvba, Belgium).

This study included 8 men and 10 women with a mean age of 79.6±8.9 years, TAVR was performed through the trans-femoral approach in 12 patients (66.7%), and through the subclavian approach in 6 patients (33.3%). The following CoreValve sizes were implanted: CoreValve 23 mm in 1 patient, CoreValve 26 mm in 6 patients, CoreValve 29 mm in 4 patients, CoreValve 31 mm in 4 patients, CoreValve Evolut R 26 mm in 1 patient and CoreValve Evolut R 29 mm in 2 patients. The average implantation depth, which was defined as the distance from the lower ventricular end of the prosthesis to the aortic valve annulus, was 4.8±0.6. Immediately after the deployment of the prosthetic valves, PVL was assessed by intra-procedural TEE, by which 6 patients (33.3%) had no PVL, 5 patients (27.8%) had trace-mild PVL, and 7 (38.9%) patients had moderate-severe PVL. In the 7 patients with significant PVL, post-deployment balloon dilation was attempted to reduce PVL. In 3 patients' (16.7%) PVL was reduced to trace or mild, while in the other 4 patients' (22.2%) PVL did not improve. Table 7 showed the detailed patient characteristics.

TABLE 7

Patient demographics.

| Age | Gender | Height | Weight | BSA | Valve Type | Valve Size | Approach | PVL after initial deployment | Ballon Dilation? | Final PVL |
|---|---|---|---|---|---|---|---|---|---|---|
| 56 | M | 185 | 158.6 | 2.7 | CoreValve | 31 | Subclavian | Mild | No | Mild |
| 95 | F | 152 | 72.3 | 1.7 | CoreValve | 23 | Femoral | Trace | No | Trace |
| 85 | F | 165 | 113.4 | 2.2 | CoreValve | 26 | Femoral | Moderate | Yes | Moderate |
| 88 | F | 163 | 54.4 | 1.5 | CoreValve | 29 | Femoral | None | No | None |
| 79 | M | 173 | 72.7 | 1.9 | CoreValve | 31 | Femoral | Moderate | Yes | Moderate |
| 84 | F | 165 | 56.8 | 1.6 | CoreValve Evolut R | 29 | Subclavian | Moderate to severe | Yes | Mild |
| 82 | M | 170 | 82.1 | 1.9 | CoreValve | 31 | Subclavian | None | No | None |
| 87 | M | 175 | 66.2 | 1.8 | CoreValve | 26 | Femoral | Mild | No | Mild |
| 73 | F | 168 | 97.8 | 2.1 | CoreValve | 25 | Femoral | Moderate | | Trace |
| 68 | F | 155 | 57.6 | 1.6 | CoreValve Evolut R | 26 | Femoral | Mild | No | Mild |
| 81 | F | 142 | 48.5 | 1.4 | CoreValve | 29 | Femoral | None | No | None |
| 86 | M | 167 | 70.3 | 1.8 | CoreValve | 31 | Subclavian | None | No | None |
| 77 | M | 12 | 83 | 2.0 | CoreValve Evolut R | 29 | Subclavian | None | No | None |
| 76 | F | 152 | 64 | 1.6 | CoreValve | 26 | Subclavian | Moderate | Yes | Moderate |
| 82 | F | 158 | 68 | 1.7 | CoreValve | 26 | Femoral | Moderate | Yes | Mild |
| 86 | M | 180 | 78.3 | 2.0 | CoreValve | 29 | Femoral | Moderate | Yes | Moderate |
| 76 | F | 165 | 69.9 | 1.8 | CoreValve | 26 | Femoral | None | No | None |
| 71 | M | 175 | 96.2 | 2.1 | CoreValve | 29 | Femoral | Trace to mild | No | Trace to Mild |

The semi-automated 3D segmentation and modeling of the aortic root took approximately 5-10 minutes. The next step to refine the 3D model and generate the STL file was automated and took less than 5 minutes. The 3D printer read in STL files from up to ten patient data in one batch, and it took a total of 9-10 hours to 12 print these ten 3D phantoms simultaneously. Post-print processing, such as removing the support materials and attaching radiopaque beads to the phantoms, took about 45 minutes for each phantom. The cost of the printing materials in each phantom was approximately $150-200.

Figure 34:
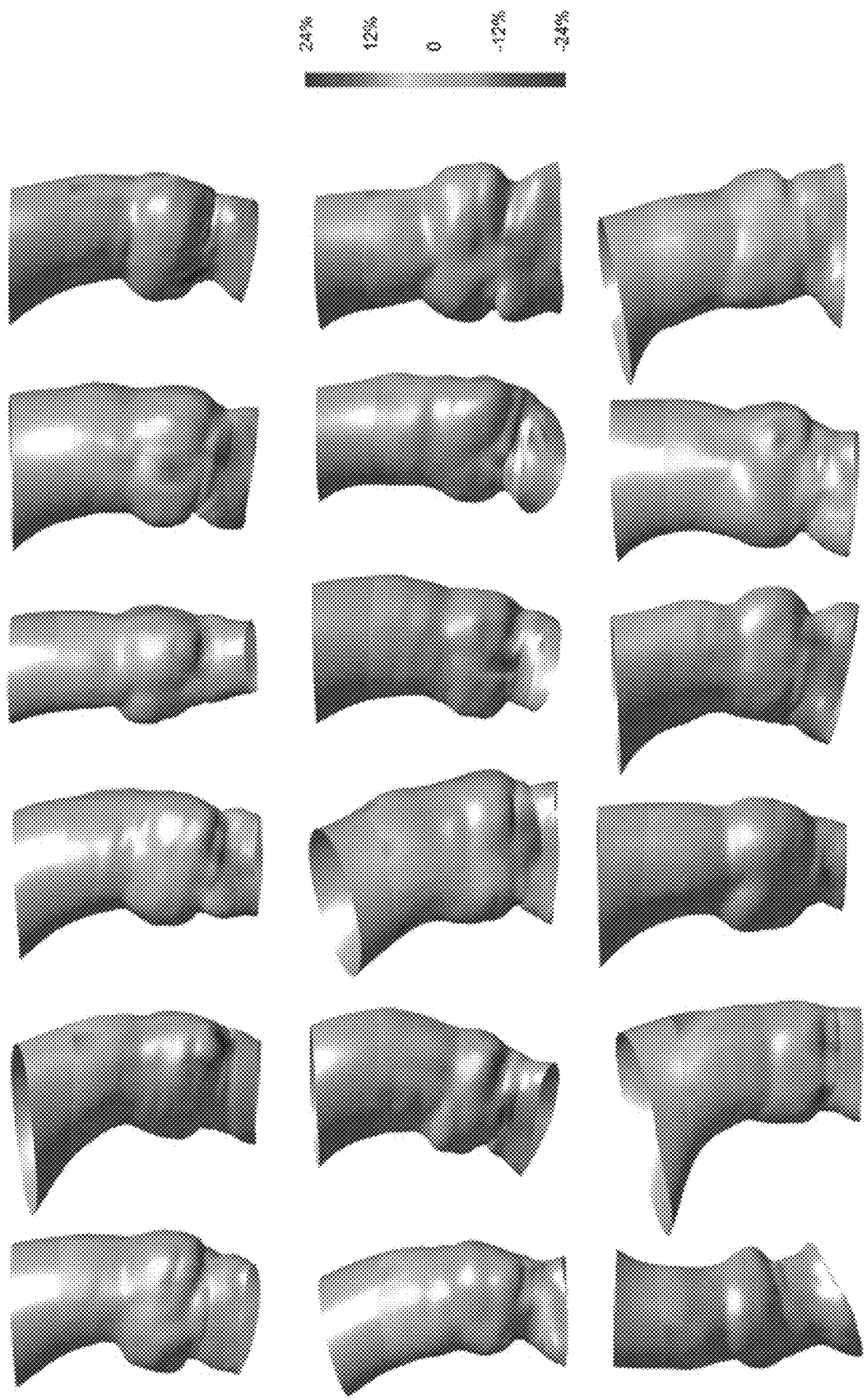
FIG. 34 illustrates the aortic root strain distributions in the 18 patients.

As shown in FIG. 34, each phantom's strain distribution showed distinctive pattern. At the annular level, the maximum, mean, and minimum circumferential strain was 15.7%±4.3%, 8.1%±3.6%, 1.3%±4.1%, respectively. As listed in Table 8, the strain was not statistically different in the three PVL subgroups. In each phantom, the maximum, mean, and minimum circumferential strain values at the annulus level were calculated. The statistics in all the patients and in each subgroup before and after the balloon post-dilation are listed.

TABLE 8

Annular circumferential strain.

| | No PVL | Trace to Mild PVL | Moderate to severe PVL | ANOVA p value | Total |
|---|---|---|---|---|---|
| Immediately after valve deployment and before balloon dilation | | | | | |
| Maximum Strain | 13.7% ± 3.3% | 18.3% ± 4.8% | 15.7% ± 4.2% | 0.22 | 15.7% ± 4.3% |
| Mean Strain | 7.3% ± 2.2% | 9.6% ± 4.3% | 7.7% ± 4.1% | 0.55 | 8.1% ± 3.6% |
| Minimum Strain | 0.7% ± 1.3% | 2.8% ± 2.9% | 0.8% ± 6% | 0.67 | 1.3% ± 4.1% |
| After balloon dilation | | | | | |
| Maximum Strain | 13.7% ± 3.3% | 17.5% ± 4.7% | 15.2% ± 4% | 0.26 | 15.7% ± 4.3% |
| Mean Strain | 7.3% ± 2.2% | 9.7% ± 3.7% | 6.1% ± 4.1% | 0.20 | 8.1% ± 3.6% |
| Minimum Strain | 0.7% ± 1.3% | 3.2% ± 2.7% | −1.6% ± 7.3% | 0.14 | 1.3% ± 4.1% |

Figure 35:
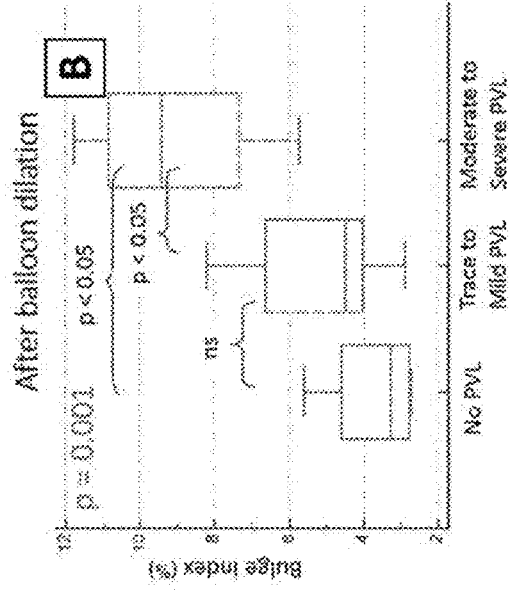
FIG. 35 illustrates the relationship between PVL and bulge index prior to balloon dilation.
Figure 36:
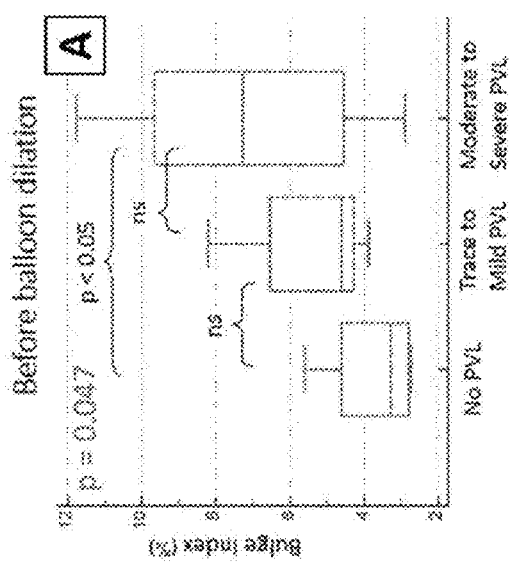
FIG. 36 illustrates the relationship between PVL and bulge index after balloon dilation.

As shown in Table 9, the maximum annular bulge index was significantly different among the three PVL subgroups (p=0.047) immediately after valve deployment, with higher bulge index being associated with the higher degree of PVL. As shown in FIGS. 35 and 36, pairwise comparison showed that the bulge index in the moderate to severe subgroup was significantly higher than that in the non-PVL subgroup only. Balloon expansion was done after initial deployment for > mild PVL in seven patients. In three of these patients' PVL improved and these were reassigned to the trace-mild subgroup. Similar to pre-balloon dilation, the maximum annular bulge index was significantly different among the three reclassified subgroups (p=0.001). But, pairwise comparison showed that the maximum bulge index in the moderate-severe PVL group was now, significantly higher than in the other two subgroups.

Figures 39, 40:
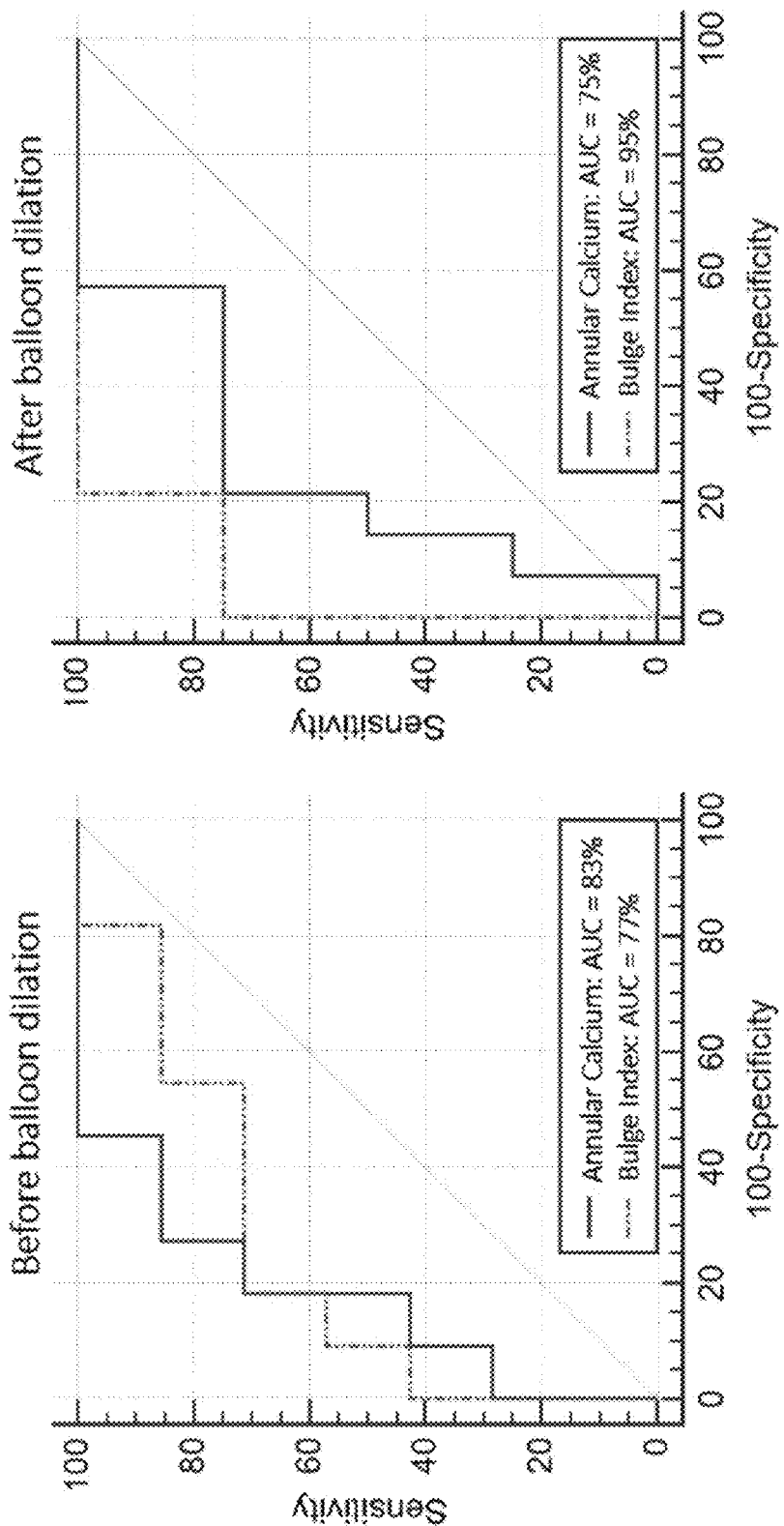
FIG. 39 illustrates the relationship between sensitivity and specificity before balloon dilation.
FIG. 40 illustrates the relationship between sensitivity and specificity after balloon dilation.

As shown in Table 10, annular calcification was the best predictor of moderate-severe PVL (ROC AUC=83%, p<0.001) immediately after initial deployment. Bulge index was a significant but less accurate predictor (AUC=77%, p=0.04). However, no other variables were predictive of PVL, and multiple logistic regression showed that the annular calcification was the only independent predictor (Cox & Snell R2=0.30, p=0.01). But, post-balloon expansion the bulge index was the only significant predictor of moderate-severe PVL (AUG=95%, p<0.0001) and annular calcium was not predictive of PVL. Furthermore, multiple logistic regression showed that the bulge index was the only independent predictor (Cox & Snell R2=0.43, p=0.001) among the variables. In FIGS. 39 & 40, the comparison of the ROC curves shows the superiority of the bulge index over annular calcium volume post-balloon dilation. In the three patients

TABLE 9

Annular bulge index compared with other known predictors of PVL.

| | No PVL | Trace to mild PVL | Moderate to Severe PVL | ANOVA p value | Total |
|---|---|---|---|---|---|
| Immediately after valve deployment and before post-TAVR dilation | | | | | |
| Annular Bulge Index | 3.7% ± 1.2% | 5.4% ± 1.7% | 7.2% ± 3.2% | 0.047 | 5.6% ± 2.7% |
| Aortic Calcium Volume * (mm3) | 670 ± 653 | 572 ± 383 | 707 ± 199 | 0.79 | 657 ± 421 |
| Annular Calcium Volume (mm3) | 59 ± 60 | 74 ± 78 | 156 ± 69 | 0.048 | 101 ± 79 |
| LVOT Calcium Volume * (mm3) | 2 ± 3 | 8 ± 9 | 37 ± 40 | 0.13 * | 17 ± 29 |
| Annular Ellipticity | 1.31 ± 0.18 | 1.27 ± 0.14 | 1.31 ± 0.07 | 0.87 | 1.30 ± 0.09 |
| Prosthesis Diameter to Annular Diameter Ratio | 1.14 ± 0.08 | 1.17 ± 0.08 | 1.17 ± 0.05 | 0.66 | 1.16 ± 0.07 |
| After post-TAVR balloon dilation | | | | | |
| Annular Bulge Index | 3.7% ± 1.2% | 5.2% ± 1.8% | 9.1% ± 2.5% | 0.001 | 5.6% ± 2.7% |
| Aortic Calcium Volume * (mm3) | 670 ± 653 | 645 ± 347 | 661 ± 109 | 0.96 | 657 ± 421 |
| Annular Calcium Volume (mm3) | 59 ± 60 | 108 ± 85 | 149 ± 78 | 0.20 | 101 ± 79 |
| LVOT Calcium Volume * (mm3) | 2 ± 3 | 8 ± 10 | 58 ± 42 | 0.07 | 17 ± 29 |
| Annular Ellipticity | 1.31 ± 0.18 | 1.30 ± 0.12 | 1.27 ± 0.06 | 0.90 | 1.30 ± 0.09 |
| Prosthesis Diameter to Annular Diameter Ratio | 1.14 ± 0.08 | 1.17 ± 0.07 | 1.18 ± 0.02 | 0.62 | 1.16 ± 0.07 |

* indicates that the Levene's test was positive, and the Kruskal-Wallis test was performed.

Figure 37:
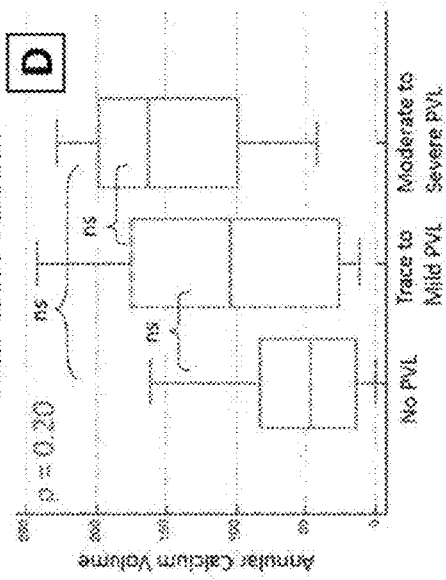
FIG. 37 illustrates the relationship between PVL and annular calcium volume prior to balloon dilation.
Figure 38:
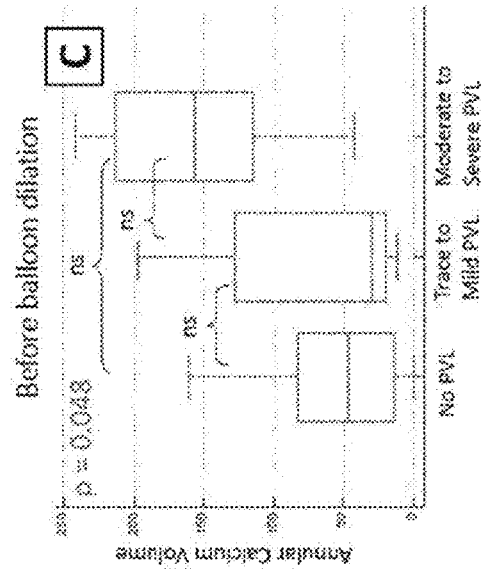
FIG. 38 illustrates the relationship between PVL and annular calcium volume after balloon dilation.

FIG. 37 illustrates the relationship between PVL and annular calcium volume prior to balloon dilation. FIG. 38 illustrates the relationship between PVL and annular calcium volume after balloon dilation. Among other quantitative parameters, only the annular calcium volume was significantly different among the subgroups (p=0.048) before balloon dilation. There was a trend for higher annular calcium volume to be associated with the higher degree of PVL, but without significant pairwise difference. However, post-balloon dilation none of these other parameters were statistically significantly different among the subgroups.

whose PVL decreased from moderate-severe to trace-mild after balloon dilation, the mean bulge index was 4.8±2.2% (3.0%, 4.2%, 7.3%) and the annular calcium volume was 165±71 ml (103 ml, 151 ml, 242 ml). In the other four patients in whom the PVL did not improve after balloon dilatation the mean bulge index was higher 9.1±2.5% (5.7%, 9.9%, 11.8%, 9.0%). But, the annular calcium volume of 149±78 ml (156 ml, 42 ml, 228 ml, 169 ml) was lower than the three who showed improvement in PVL after balloon dilatation.

TABLE 10

T-test and ROC analysis of the annular bulge index in predicting dichotomized PVL, compared with other known predictors.

| | <Moderate PVL | ≥Moderate PVL | T-test p value | ROC AUC | ROC p value | ROC cutoff | Sensitivity | Specificity |
|---|---|---|---|---|---|---|---|---|
| Immediately after valve deployment and before post-TAVR dilation | | | | | | | | |
| Annular Bulge Index | 4.5% ± 1.6% | 7.2% ± 3.2% | 0.03 | 76.6% | 0.04 | 0.056 | 71.43 | 81.82 |
| Aortic Calcium Volume | 626 ± 524 | 707 ± 199 | 0.65 | 59.7% | 0.5 | 356 | 100 | 45.45 |
| Annular Calcium Volume | 59 ± 60 | 156 ± 69 | 0.0001 | 83.1% | 0.0007 | 83 | 85.71 | 72.73 |
| LVOT Calcium Volume | 2 ± 3 | 37 ± 40 | 0.07 | 72.7% | 0.11 | 8.6 | 57.14 | 90.91 |
| Annular Ellipticity | 1.29 ± 0.15 | 1.31 ± 0.07 | 0.82 | 57.1% | 0.62 | 1.25 | 85.71 | 54.55 |
| Prosthesis Diameter to Annular Diameter Ratio | 1.16 ± 0.08 | 1.17 ± 0.05 | 0.60 | 55.8% | 0.69 | 1.14 | 85.71 | 54.55 |
| After post-TAVR balloon dilation | | | | | | | | |
| Annular Bulge Index | 4.6% ± 1.7% | 9.1% ± 2.5% | 0.0006 | 94.6% | <0.0001 | 0.056 | 100 | 78.57 |
| Aortic Calcium Volume | 656 ± 479 | 661 ± 109 | 0.97 | 51.8% | 0.90 | 441 | 100 | 50 |
| Annular Calcium Volume | 87 ± 77 | 149 ± 78 | 0.17 | 75% | 0.07 | 151 | 75 | 78.57 |
| LVOT Calcium Volume | 5 ± 8 | 58 ± 42 | 0.09 | 80.4% | 0.12 | 24 | 75 | 100 |
| Annular Ellipticity | 1.31 ± 0.14 | 1.27 ± 0.06 | 0.65 | 57.1% | 0.63 | 1.33 | 100 | 42.86 |
| Prosthesis Diameter to Annular Diameter Ratio | 1.16 ± 0.08 | 1.18 ± 0.02 | 0.51 | 60.7% | 0.42 | 1.15 | 100 | 57.14 |

Figure 3:
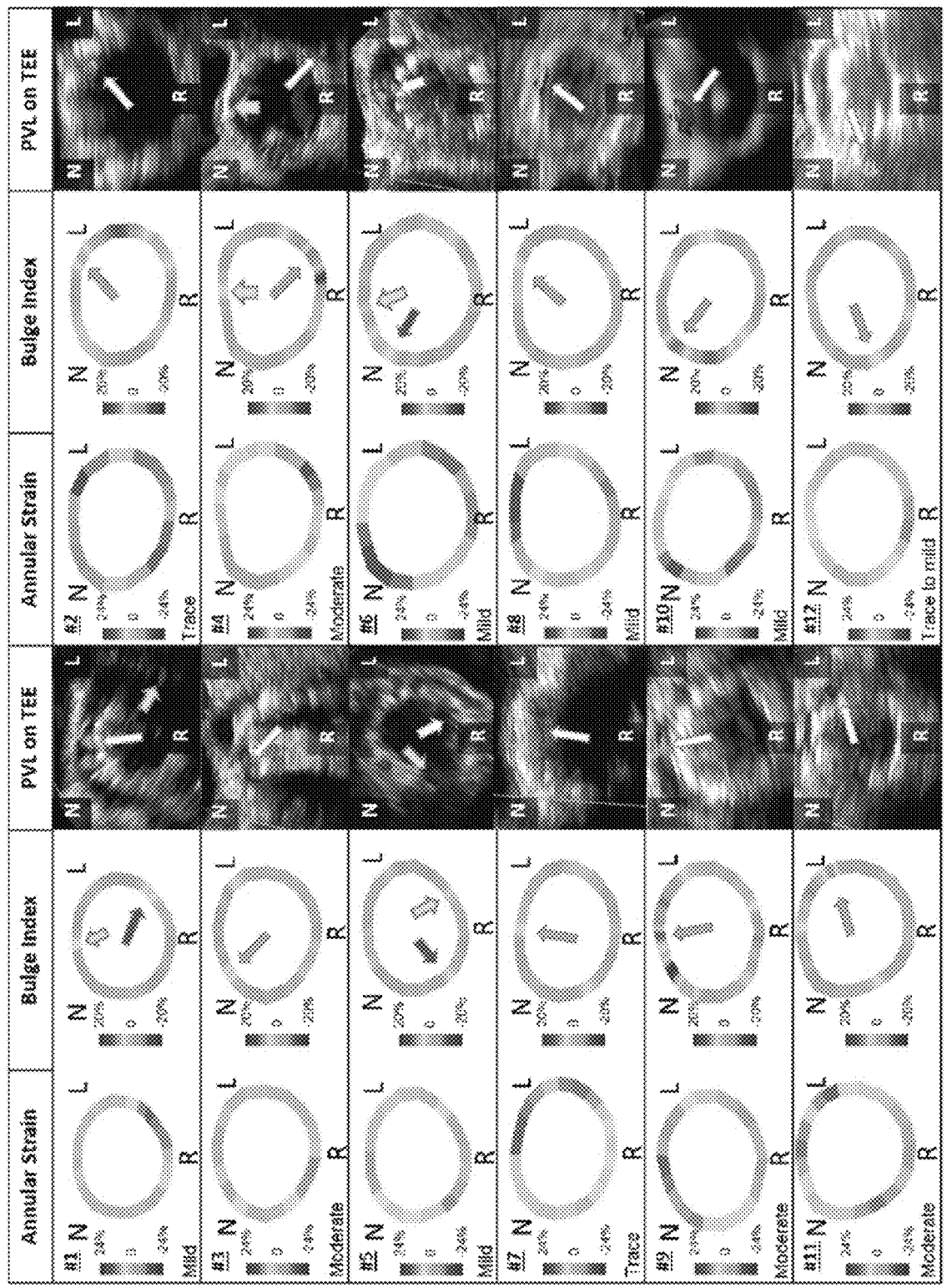
FIG. 3 illustrates the prediction of the PVL locations in 12 patients who had any degree of post-TAVR PVL.
Figure 7A:
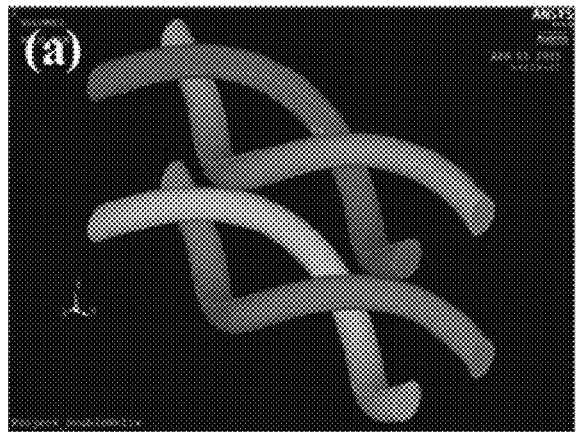
FIG. 7($a$)-($d$) depicts an ANSYS model and meshing of the DH design for the FEA simulations.
Figure 7B:
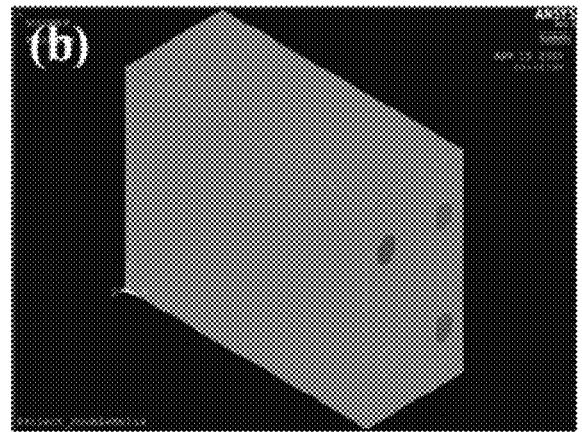
Figure 7C:
Figure 7D:
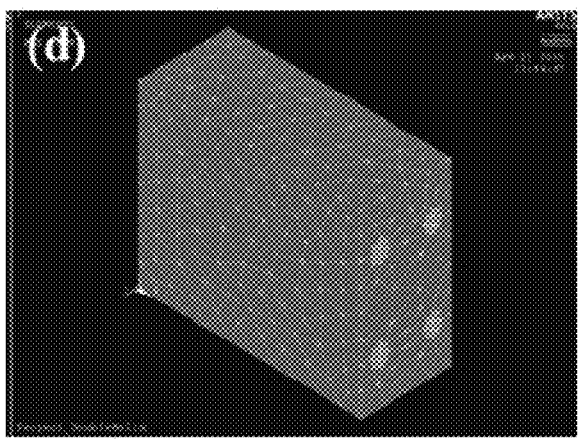
Figure 8A:
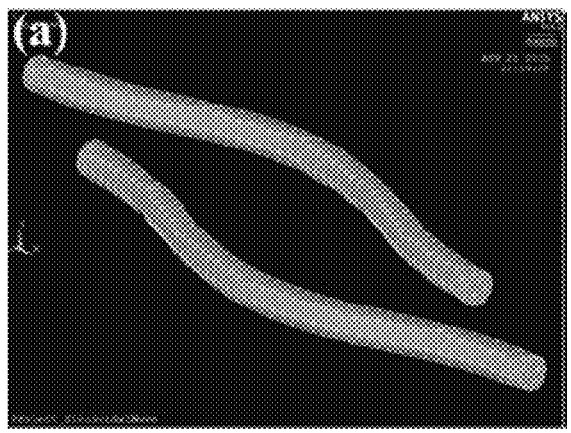
FIG. 8($a$)-($d$) depicts the shape and the von Mises stress in the wavy fibers at strain levels of (a) 0%, (b) 2%, (c) 4%, and (d) 8%.
Figure 8B:
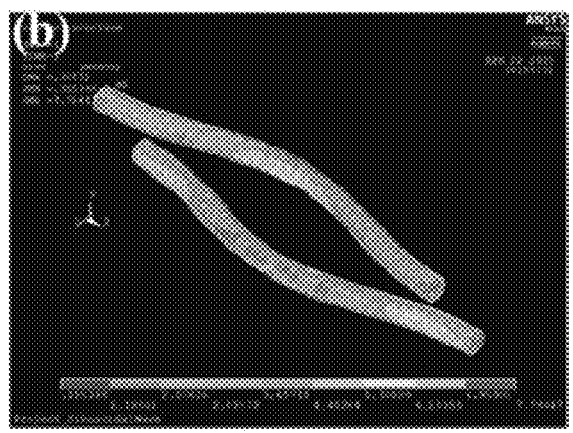
Figure 8C:
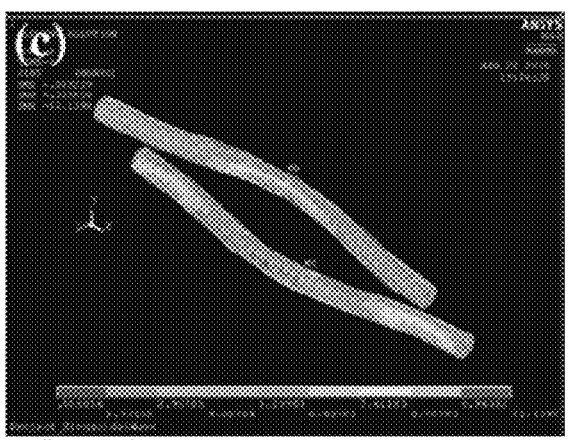
Figure 8D:
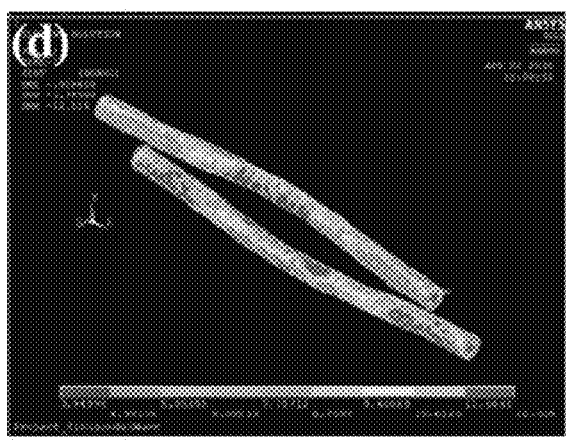

FIG. 3 shows the locations of the final PVL in the 12 patients who had any degree of PVL after TAVR and the sites of the maximum annular bulge index. The latter predicted the location of the dominant PVL in 9 patients (accuracy=75%). In patients #1 and #5, who had multiple PVL sites, the second largest bulge index position predicted the dominant PVL location, while the maximum bulge index predicted a minor PVL site. In patient #6, the annular strain distribution showed multiple high bulges (indicated by the warm color) besides the maximum bulge site, and only one of them predicted PVL.

The invention claimed is:

1. A physical model representative of biological soft tissue having anisotropic properties comprising:
   a primary material in the shape of the modeled biological soft tissue; and
   one or more structures of a secondary material within the primary material;
   wherein the primary material has an elastic modulus;
   wherein each structure of the secondary material has a shape;
   wherein the shape of at least one structure of the secondary material is selected from the group consisting of a sinusoidal wave, a double helix, and an interlocking chain;
   wherein the shape of each structure of the secondary material is selected so that the elastic modulus of the physical model of the primary and secondary materials is greater than the elastic modulus of the primary material; and
   wherein the physical model has anisotropic properties that approximate the anisotropic properties of the biological soft tissue being modeled.

2. The physical model of claim 1, wherein the modeled biological soft tissue is an organ.

3. A method for forming the physical model of claim 1 comprising:
   creating an initial computer model representative of the biological soft tissue;
   computing an initial elastic modulus of the initial computer model representative of the biological soft tissue;
   creating a subsequent computer model representative of the biological soft tissue by increasing the initial elastic modulus to a subsequent elastic modulus of the subsequent computer model; and
   printing the physical model of the biological soft tissue with the primary and secondary materials based on the subsequent computer model.

4. The method of claim 3, wherein the modeled biological soft tissue is an aortic valve.

5. The method of claim 3, wherein creating the initial computer model representative of the biological soft tissue is derived from diagnostic imaging of a patient.

6. The method of claim 3, wherein the shape of each structure of the secondary material is selected from the group consisting of a sinusoidal wave, a double helix, and an interlocking chain.

7. A method for testing a surgical procedure using the physical model of claim 1 comprising:
   creating an initial computer model representative of the biological soft tissue;
   computing an initial elastic modulus of the initial computer model representative of the biological soft tissue;
   creating a subsequent computer model representative of the biological soft tissue by increasing the initial elastic modulus to a subsequent elastic modulus of the subsequent computer model;
   printing the physical model of the biological soft tissue with the primary and secondary materials based on the subsequent computer model;
   inserting a prosthesis into the printed physical model; and
   evaluating the performance of the prosthesis in the printed physical model.

8. The method of claim 7, wherein the modeled biological soft tissue is an aortic valve.

9. The method of claim 8, wherein evaluating the performance of the prosthesis comprises:
   circulating a fluid through the printed physical model; and
   evaluating the prosthesis for paravalvular leakage.

10. The method of claim 7, wherein the prosthesis is an aortic valve replacement.

11. The physical model of claim 1, wherein the primary material comprises an elastic metamaterial.

12. The physical model of claim 1, wherein the secondary material comprises a metamaterial that is stiffer than the primary material.

13. The physical model of claim 1, wherein each of the structures of the secondary material have the same shape.

14. The physical model of claim 1, wherein each of the structures of the secondary material are embedded in the primary material.

15. The physical model of claim 1, wherein the modeled biological soft tissue is an aortic valve.

16. The physical model of claim 1, wherein the shape of each structure of the secondary material is selected from the group consisting of a sinusoidal wave, a double helix, and an interlocking chain.

17. The physical model of claim 1, wherein the physical model comprise a physical model printed using a multi-material 3-D printer.

18. A physical model representative of an organ comprising:
 a primary elastic metamaterial in the shape of the modeled organ; and
 one or more structures of a secondary material embedded in the primary elastic metamaterial, wherein the secondary material comprises a metamaterial that is stiffer than the primary elastic metamaterial;
 wherein the primary elastic metamaterial has an elastic modulus;
 wherein each structure of the secondary material has a shape;
 wherein the shape of each structure of the secondary material is selected so that the elastic modulus of the physical model of the primary elastic metamaterial and secondary materials is greater than the elastic modulus of the primary material; and
 wherein each of the structures of the secondary metamaterial has a shape selected from the group consisting of a sinusoidal wave, a double helix, and an interlocking chain.

19. The physical model of claim 18, wherein each of the structures of the secondary metamaterial have the same shape.

20. The physical model of claim 18, wherein the physical model comprise a physical model printed using a multi-material 3-D printer.

* * * * *